United States Patent [19]

Touitou

[11] Patent Number: 5,540,934
[45] Date of Patent: Jul. 30, 1996

[54] COMPOSITIONS FOR APPLYING ACTIVE SUBSTANCES TO OR THROUGH THE SKIN

[76] Inventor: Elka Touitou, 6 Demumit, Givat Canada, Gilo, Jerusalem 93890, Israel

[21] Appl. No.: 264,204

[22] Filed: Jun. 22, 1994

[51] Int. Cl.$^6$ .................................................. A61K 9/127
[52] U.S. Cl. .............................. 424/450; 424/401; 424/63
[58] Field of Search ................................. 424/450, 401, 424/63

[56] References Cited

U.S. PATENT DOCUMENTS

| | | | |
|---|---|---|---|
| 4,761,288 | 8/1988 | Mezei | 424/450 |
| 4,994,213 | 2/1991 | Aitcheson | 264/4.6 |
| 5,004,611 | 4/1991 | Leigh | 424/450 |
| 5,077,057 | 12/1991 | Szoka | 424/450 |
| 5,154,930 | 10/1992 | Popesur | 424/489 |

OTHER PUBLICATIONS

Touitou et al., International Journal of Pharmaceutics, Modulation of Caffeine Skin . . . , 103 (1994) 131–136.
Touitou et al., Journal of Pharmaceutical Sciences, Liposomes as Carriers for . . . , vol. 83, No. 9, Sep. 1994.
Riaz et al., Riaz, Weinr, and Martin, Liposomes, Chapter 16, pp. 568–603.
Roding, Seifen Ole Fetle Wachse 116, 1990.
Cooper J. Pharmaceutical Science 73, 1984.
Batzri et al. Single Bilayer Liposomes Prepared Without Sonication, Biochim. Biophys. Acta. 298 (1973) 1015–1019.
Kremer et al. Vesicles Of Variable Diameter Prepared By A Modified Injection Method, Biochemistry 16 (1977) pp. 3932–3935.
Barry, V. W. Optimizing Percutaneous Absorption. In Bronaugh, R. L and Maibach, M. I. (Eds). Percutaneous Absorption, Dekker, New York, 1989, pp. 531–565.
Riaz et al. In Pharmaceutical Dosage Forms. Disperse Systems, vol. 2; Lieberman, H. A., Rieger, M. M., Banker, G. S., Eds, Marcel Dekker, Inc. New York and Basel, 1988 pp. 567–602.
Touitou et al. Altered Skin Permeation Of A Highly Lipophilic Molecule: Tetrahydrocannabinol. Int. J. Pharm. 43 (1988) 17–22.
Touitou et al. Enhanced Permeation Of Theophylline Through The Skin And Its Effect On Fibroblast Proliferation. Int. J. Pharm. 70 (1991) 159–166.

*Primary Examiner*—Gollamudi S. Kishore
*Attorney, Agent, or Firm*—Keck, Mahin & Cate

[57] ABSTRACT

A cosmetic or medical composition for topical application to the skin. It results in the transdermal passage of an active ingredient, or in the introduction of such agent into the skin. The essential components of such compositions are a phospholipid, a lower aliphatic alcohol of two to four carbon atoms, optionally with propylene glycol, water and a compatible active ingredient. The alcohol content is generally from 20 to 50%, and when propylene glycol is present, the combined percentage of alcohol and glycol being up to about 70%. The composition are suitable for the topical application of a wide variety of cosmetic and pharmaceutical compounds.

5 Claims, 3 Drawing Sheets

COMPOSITIONS FOR APPLYING ACTIVE SUBSTANCES TO OR THROUGH THE SKIN

FIELD OF THE INVENTION

The invention relates to novel compositions containing phospholipids, short chain alcohols (C2–C4) and water. These compositions may also contain polyols. Prefered compositions contain phospholipids, ethanol (EtOH), water (DDW), and propylene glycol (PG).

This invention relates to pharmaceutical, cosmetic, veterinary or phytopharmaceutical compositions for delivery to skin, membranes, or tissues, which enhance the delivery of the active agent at the site of application, where the agent may form a reservoir in the skin (membrane, tissue) or may be absorbed systemically into the blood circulation.

The compositions are hydro-alcoholic or hydro/alcoholic/glycolic phospholipid systems in which the concentration of alcohols, glycols, or their combination is relatively high. The main components of these systems are: phospholipids [with various chemical structures like phosphatidylcholine (PC), hydrogenated PC, phosphatidic acid (PA), phosphatidylserine (PS), phosphatidylethanolamine (PE), phosphatidylglycerol (PPG), phosphatidylinositol (PI), hydrogenated PC and others, ethanol (or other short chain alcohols), water and propylene glycol (or other glycols).

The novel compositions enable the delivery of higher concentrations of active agent to/through a membrane (skin). The delivery can be modulated by changes in alcohol:water or alcohol-polyol:water ratio.

STATE OF THE PRIOR ART

In drug delivery, there are known a number enhancing agents, some used in research and some on the market, for promoting and increasing the amount of drug delivered to/through the skin. Examples of these enhancing agents are: DMSO, pyrrolidone derivatives, n-decylMSO, some surfactants, oleic acid, ethanol, Azone®, and others (Barry, 1989).

Phospholipids are known for their broad use in liposomal systems as well as emulsifiers in the preparation of emulsions. All these systems used for pharmaceutical or cosmetic purposes are aqueous systems with small if any concentration of alcohol and/or glycol for preservation and/or improving texture of the formulation.

Emulsions containing phospholipids are prepared by mixing an aqueous and an oily phase, in some cases followed by use of an homogenizer.

Preparation of liposomal systems involves the use of organic solvents such as chloroform, alcohols and others. In some methods of preparation, an organic phospholipid solution is evaporated to form a lipidic film, which is then hydrated to give an aqueous vesicular system (Riaz et al, 1988). In an alternative method, liposomes are prepared by injecting an ethanolic solution of lipid into an aqueous solution, resulting in a dilute ethanolic solution (2.5–7.5% ethanol) (Batzri et al, 1973). The alcohol is then removed by different means such as dialysis (Kremer et al, 1977). The alcohol, if present is in low concentrations only, less than about 20% in the final product (e.g. 7.5%, Kremer et al, 1977).

SUMMARY OF THE INVENTION

The invention relates to compositions which are hydro/alcoholic or hydro/alcoholic/glycolic phospholipid systems in which the concentration of alcohol or its combination with polyol is relatively high. We call these compositions: Ethosomal systems.

The systems described in this invention are pharmaceutical, cosmetic, phytopharmaceutical or veterinary compositions for application to the skin (or other tissues) comprised of combinations of phospholipids, alcohols, water and glycol (polyols), as major components.

An ethosomal system is a skin permeation enhancing system which has the potential to form ethosomes, which are "soft" vesicles formed from phospholipid in the presence of water and ethanol (alcohol) and sometimes glycols (polyols). The size of the vesicles depends on the water: alcohol ratio.(see appendixes 1–6) and on the phospholipid concentration. On the skin, the ethosomes change their size by fusing together as a result of the change in solvent ratio. In the preparation, the vesicle size does not change since the ratio between the solvents is constant. Penetration and evaporation of the following application to the skin allows the transition from small to large vesicles, which grow in size until a film is formed.

An important characteristic of ethosomes is enhanced membrane permeability for various compounds. Ethosomal systems, vesicular in nature, depending on the ratio of the components and the chemical structure of the phospolipids, can be comprised of very small entities (nm's) up to larger vesicles (mm's) (see appendixes 1–6). High alcoholic (organic solvent) concentration favors the production of ethosomes in nm's range while high aqueous and phospholipid concentrations favorize the formation of large size ethosomes. As examples formulation 503 (Table 2) containing 68% organic solvent and 30% water has a mean population of less than 10 nm's, while formulation 510 containing 50% organic solvent and 48% water has a mean population of 1 mm. In system 503 the concentration of ethanol was 48% while in formulation 510 the ethanol concentration is only 20%, showing that the alcohol concentration is of great importance in determining vesicle size. The phospholipids which can be used are: phosphatidylserine (PC), phsophatidylserine (PS), phosphatidic acid (PA), phosphatidylethanolamine (PE), phosphatidylglycol (PPG), hydrogenated PC and others. Some prefered phospholipids are soya phospholipids such as Phospholipon 90 (PL-90). The concentration of phospholipid ranges between about 0.5–10% w/w. Cholesterol at concentrations ranging between about 0.1–1% can also be added to the preparation. Examples of alcohols which can be used are: ethanol and isopropyl alcohol. Examples of glycols are propylene glycol and Transcutol®. The source of the phospholipids can be egg, soybean, semi-synthetics, and synthetics. Non ionic surfactants can be combined with the phospholipids in these preparations e.g. PEG-alkyl ethers (Brij-52). Cationic lipids like cocoamides, POE alkyl amines, dodecylamine, cetrimide and like.

The concentration of alcohol (EtOH etc.) in the final product ranges from about 20–50%. The concentration of the non-aqueous phase (alcohol and glycol combination) may range between about 22 to 70%. The rest of the carrier contains water and possible additives.

Vesicle formation is dependent on the water: alcohol ratio. This ratio is kept constant in the product, therefore, no changes in the entities population occur. Nevertheless, penetration and evaporation of the alcohol following application to the skin allows the transition from small vesicles to a larger ones, finally resulting in film formation.

In contrast to the present state of the art where "tough" liposomes accomplished by addition of different substances like cholesterol to the phospholipids and in absence of alcohol, this invention relates to "soft" vesicles, that can be easily formed in a hydroalcoholic medium. One of the important properties of these systems is that small entities can penetrate into the skin, while larger vesicles can form a reservoir in the skin and a film on the skin surface as a result of solvent evaporation taking place after the application.

These carriers can be used to deliver various active agents such as: Peptides, Anti-aging agents, tanning agents, and vitamins, Antiviral drugs, Psoriasis treatment agents, Hormones, Medicinally active componenets of plants such as oleoresins, volatile oils, glycosides, alkaloides, terpenes and others.

Examples of active agents which can be used with these systems are as follows: drugs like nicotine, nitroglycerine, estradiol (or like), testosterone (or like), progesterone, nifedipine, minoxidil, tetrahydrocannabinol (THC) or other cannabinoids, xanthines, anxiolytics (diazepam and others), antiepileptic (valnoctamide and others), diclofenac (and other NSAIDs), Antibiotics, corticosteroids, tocopherol, 5-FU, acyclovir, colchicine and other antimytotic agents, prazosin and other antihypertensive agents, papaverine, miconazole nitrate, ketoconazole and other antifungals, enzymes like SOD; peptides, hydroxy acids and amino acids.

DETAILED DESCRIPTION OF THE PREFERRED EMBODIMENTS

In Vitro Skin Penetration/Permeation Measurements

Skin permeation experiments were carried out in our laboratory as previously described (Touitou and Fabin, 1988; Touitou et al, 1991).

Full Thickness Skin

The animals used in these investigations were hairless mice obtained from the Weizmann Institute, Rehovot, Israel. The skin of 5–7 week old male mice was excised before the experiment, examined for integrity and cut for diffusion cell assembly. In most of the experiments, the skin from the abdominal site was used.

In Vitro Permeation Experiments in Horizontal Diffusion Cells

The Valia-Chien cell assembly was used to perform the experiments on permeation of the drugs from various donor compositions through hairless mouse skin and the concentration in the skin. Mouse skin treated as described above was mounted in cells with a surface area of 0.64 cm$^2$ and half-cell volume of 3 ml. The receiver compartments contained a medium (hydroalcoholic, water, or buffer solutions) for ensuring pseudo-sink conditions. During the experiment, samples were withdrawn and mixed with scintillation cocktail (Packard, USA) and assayed in the Kontron Betamatic Scintillation Counter (Lumitron Scientific Industries) or directly assayed by HPLC. The sample volumes were replaced with fresh solution. The results were treated using the "Transderm" computer program (Touitou and Fabin, 1988). Each experiment was tetraplicated. The two-tailed, paired Wilcoxon test was used for determining the statistical significance of the effect of enhancers on the permeability coefficient changes. For these analyses, the "Balance" (IBM) computer program was used.

Skin Permeation Determination in Franz Cells

The permeation flux of drugs and the quantity of drug in the skin from the test system was measured in vertical cells (Franz diffusion cells). The experimental system conditions were: receiver temperature 37° C. and receiver volume 4–8 ml. The samples were assayed either by scintillation counting or by HPLC. The results are presented as a mean of 4 experiments and were analyzed by Transderm and by Balance (IBM) computer programs.

Size Distribution of Liposomes

The size distribution of ethosomes was measured in a Malvern autosizer (Malvern). (See appendixes 1–4).

Method of Preparation and Compositions

Examples of compositions are given in Tables 1 and 2.

a) Ethosomal system containing a relatively high concentration of Ethanol or Ethanol and Propylene Glycol was obtained as follows:

A lipophilic drug(10%) and PL-90(5%) were dissolved in an EtOH-PG(62.4%) mixture at room temperature. DDW(22.6%) was then added with vigorous stirring.

See example II-Immune agent.

b) Ethosomal systems containing a relatively high concentration of Ethanol (20–50%) or Ethanol and Propylene Glycol (22–70%) were obtained as follows:

PL-90 (0.5–10%) was dissolved in the EtOH-PG mixture. Hydrophilic drugs were dissolved in DDW and added to the PL-90 solution.

c) Ethosomal system was prepared by mixing (Heidolph mixer) PL-90 and water in concentrations as in "b" and heating to dispersion at 60°–70° C. The dispersion was then cooled (ice bath) with constant mixing for 30 minutes. To the above dispersion a solution of 2% Minoxidil in ethanol-propylene glycol (concentration as above) was added with vigorous mixing. A vesicular system was obtained. The preparation may be passed through a homogenizer (like Gaoline).

d) Minoxidil ethosomes were prepared by gently heating or at room temperature, a solution of soybean lecithin (Phospholipon 90) and Minoxidil in a propylene glycol ethanol mixture. Distilled water or buffer solution was added to the above system. A vesicular system was formed. The preparation may be passed through a homogenizer (like Gaoline). concentrations of ingredients as in "c".

e) A vesicular system containing a relatively high concentration of Ethanol or Ethanol and Propylene Glycol was obtained as follows: A dispersion containing soya phospholipid (Phospholipon 90), Minoxidil, Ethanol, propylene glycol, double distilled water or buffer solution, is passed through a homogenizer in order to reduce particle size. concentrations of ingredients as in "c".

f) Composition and preparation as described in a–c but containing 0.2% cholesterol in addition.

g) As in a–d where mixtures of phospholipids are used.

h) The vesicular systems can be incorporated in various carriers such as: PVP/VA (gels, membranes, solutions), PVP (gels, membranes, solutions) carbomer gels, polaxomer (gels, solutions), emulsions, creams, Pluronic F127 or Tetronic gels and the like, cellulose derivatives gels, PL-90ant extract gels (aloe vera gel etc), and the like.

TABLE 1

Examples of skin permeation enhancing systems Containing various drugs

| | Systems | | | | | | | | | |
|---|---|---|---|---|---|---|---|---|---|---|
| | DYPH1 | DYPH2 | MND200 | SOD | Immune | THC 1 | MM33 | MM39 | MM42 | MM43 |
| COMPONENTS | | | | | | | | | | |
| DYPHYLLINE | 1% | 1% | | | | | | | | |
| ACYCLOVIR | | | | | | | | | | |
| DICLOFENAC | | | 7 μCi/ml | | | | | | | |
| SOD | | | | 6% | | | | | | |
| ROQUINIMEX | | | | | 10% | | | | | |
| MINOXIDIL | | | | | | | 2% | 2% | 2% | 2% |
| THC | | | | | | 7 μci/ml | | | | |
| PL-90 | 5% | 5% | 2% | 2% | 5% | 2% | 2% | 2% | 5% | 5% |
| CHOLESTEROL | — | — | — | — | — | — | — | — | — | 0.1% |
| PG | 18.8% | — | 19.6% | 18.4% | 31.2% | 19.6% | 19.2% | 19.2% | 19.5% | 18.6% |
| DDW | 47% | 47% | 49% | 46% | 22.6% | 29.4 | 28.8% | 48% | 48.8% | 27.9% |
| EtOH | 28.2% | 47% | 29.4% | 27.6% | 31.2% | 49% | 48% | 28.8% | 29.3% | 46.5% |

Examples of Compositions and Preparation Methods

Example I—SOD Ethosomal Preparation

| A) | Amerchol L-101 | 57.1% | 4 parts |
|---|---|---|---|
| | Amerlate P | 14.3% | 1 part |
| | Brij 52 | 28.6% | 2 parts |
| B) | Carbopol 934P | 1% | |
| | DDW | 98% | |
| | TEA | 1% | |
| | SOD | 6% | |
| C1) | PL-90 | 2% | |
| | DDW | 46% | |
| C2) | EtOH 3 | 27.6% | |
| | PG | 18.4% | |

Gel Preparation
1. Preparation of "A" by melting the ingredients in a water bath. Cool while stirring.
2. Disperse Carb 934 P in DDW at room temperature.
3. Mix A and B in the ratio of 7% of A with 93% B and add TEA.

System Preparation
4. SOD was dissolved in a PL-90 dispersion in DDW [obtained by heating in a water bath of 70° C. with constant mixing (C1)].
5. An EtOH:PG mixture (C2) was prepared and added to C1 with vigorous mixing and cooling in an ice bath.

| Final formulation: | |
|---|---|
| 6. Mix gel with the system in a 1:1 ratio. | |
| Drug | 3% |
| Lipid phase (A) | 3.5% |
| Gel (B) | 46.5% |
| PL-90 + DDW (C1) | 22% |
| PG + EtOH(C2) | 25% |

Example II—IMMUNE AGENT
(ROQUINIMEX)Ethosomal Preparation

| A) Pluronic F127 | 40% |
|---|---|
| DDW | 60% |
| B) ROQUINIMEX | 10% |
| PL-90 | 5% |
| EtOH 95% | 31.2% |
| PG | 31.2% |
| DDW | 22.6% |

Prepare a Pluronic gel of 40% in DDW. Dissolve Roquinimex and PL-90 in the EtOH-PG mixture. Add DDW to the latter with vigorous stirring.
Add B to A with vigorous stirring, at a ratio of 1:1.

Example III—THC Ethosomal Preparation

| THC | 1% |
|---|---|
| PL-90 | 4.2% |
| EtOH | 51.7% |
| PG | 15% |
| PVP-VA S-630 | 12.5% |
| DDW | 16.6% |

THC and PL-90 were dissolved in an EtOH-PG mixture with gentle heating while mixing. DDW was added with continuous stirring. PVP-VA was slowly added while stirring. The preparation was sonicated in 3 cycles of 5 minutes with 5 minutes rest between each cycle.

Example IV—Minoxidil Ethosomal Preparation
(MM50-G)

| A) Carbopol 934P | 0.75% |
|---|---|
| Ethomeen C/15 | 0.75% |
| DDW | 73.5% |
| EtOH | 25% |
| B) Minoxidil | 4% |
| PL-90 | 5% |
| EtOH 95% | 40% |
| PG | 20% |
| DDW | 31% |
| Tocopherol | 0.02% |
| MM50-G, Final concenrations: | |
| Carbopol 934 P | 0.38% |

| | |
|---|---|
| Ethomeen C/15 | 0.38% |
| Minoxidil | 2% |
| PL-90 | 2.5% |
| EtOH (95%) | 32.5% |
| PG | 10% |
| DDW | 52.3% |

Carbopol gel was prepared by dispersing Carbopol 934 P in DDW and Ethomeen was added. Ethanol was added to obtain an hydroalcoholic gel. The drug, antioxidant, and PL-90 were dissolved in the EtOH-PG mixture with gentle heating (30° C.). DDW was added with vigorous stirring to obtain the system.

The system may be homogenized.

B was added to A at a 1:1 ratio.

The mean size of vesicles was found to be 35 nm

Example V—Minoxidil Ethosomal Preparation (MM)

As in example IV (MM50-G) with the following variations:

The gel:system ratio may be changed to 1:2, 1:3, or 1:4.

The ratio between solvents can be changed: EtOH (25–49%), PG (0–20%), and DDW (25–49%) can be changed.

The PL-90 concentration can be raised to about 10%.

Example VI—DICLOFENAC SODIUM Ethosomal Preparation

| | |
|---|---|
| Diclofenac sod. | 1% |
| PL-90 | 1% |
| Carbopol 934 | 0.9% |
| Ammonium 10% soln. | 1.8% |
| EtOH | 21.9% |
| DDW | 68.9% |
| PG | 4.16% |

Example VII—ACYCLOVIR Ethosomal Preparation

| | |
|---|---|
| Acyclovir | 5% |
| Ammonium 10% soln. | 1.66% |
| Carbopol 934 | 0.83% |
| PL-90 | 2.5% |
| DDW | 58.3% |
| EtOH | 27.5% |
| PG | 4.16% |

TABLE 2

| Sys No. | Ingredient, % w/w | | | | | |
|---|---|---|---|---|---|---|
| | PL-90 | DDW | EtOH | PG | Other | Method* |
| 500 | 2 | 48 | 30 | 20 | | Hot |
| 501 | 2 | 48 | 30 | 20 | | Cold |
| 502 | 2 | 30 | 48 | 20 | | Hot |
| 503 | 2 | 30 | 48 | 20 | | Cold |
| 504 | 5 | 45 | 30 | 20 | | Hot |
| 505 | 5 | 45 | 30 | 20 | | Cold |
| 506 | 5 | 30 | 45 | 20 | | Hot |
| 507 | 5 | 30 | 45 | 20 | | Cold |
| 508 | 2 | 30 | 38 | 30 | | Cold |
| 509 | 2 | 38 | 30 | 30 | | Cold |
| 510 | 2 | 48 | 20 | 30 | | Cold |
| 511 | 1.8 | 30 | 38 | 30 | 0.2(M(–)*) | Cold |
| 512 | 5 | 30 | 45 | 20 | | Cold |
| 513 | 5 | 35 | 30 | 30 | | Cold |
| 514 | 2 | 33 | 30 | 30 | 5(Brij52) | Cold |
| 515 | 17 | 26 | 40 | 17 | | Cold |
| 516 | 9.3 | 44.4 | 27.7 | 18.5 | | Cold |
| 517 | 5 | 20 | 40 | 40 | 5(Brij52) | Cold |
| 518 | 2 | 47 | 30 | 20 | 1(Col**) | Cold |
| 525 | 10 | 64 | 26 | 0 | | Hot |
| 529 | 1.7 | 55.4 | 34.3 | 8.6 | | Cold |

PL-90: phospholipid; DDW: water; Etoh: ethanol; PG: propylene glycol
*M(–): l-Menthol
**Col: Colchicine
*See "Hot" or "Cold" methods described below.

"Cold" method

Phospholipid is dissolved in ethanol at room temperature by vigorous stirring with the use of Heidolph mixer. Propylene glycol is added during the stirring. The mixture is heated to 30° C. in a water bath. The water heated to 30° C. in a separate vessel is added to the mixture which is then stirred for 5 minutes in a covered vessel.

"Hot" method

The phospholipid is dispersed in water by heating in a water bath at 40° C. until a colloidal solution is obtained. In a seperate vessel ethanol and propylene glycol are mixed and heated to 40° C. Once both mixtures reach 40° C. the organic phase is added to the aqueous one.

During the preparation process the drug is dissolved in water or in ethanol depending on its hydrophilic/hydrohpobic properties.

EXAMPLES OF SKIN PERMEATION PARAMETERS OF VARIOUS DRUGS FROM THESE SYSTEMS (Kp=permeability coefficient; $Q_{skin}$=quantity of drug in the skin at the end of the experiment; $Q_{rec}$=quantity of drug in the receiver compartment of the cell at the end of the experiment) Kp reflects the permeation through the skin and Qs reflects the reservoir formation in the skin.

Example VIII

| | MM33= MM36 vs. (see Table 1) | blank MM (= Minoxitrim$^R$, Trima, Israel) 2% minoxidil |
|---|---|---|
| Kp= | $1.36 \times 10^{-2}$ cm*hr$^{-1}$ | $8.84 \times 10^{-4}$ cm*hr$^{-1}$ |
| $Q_{skin}$= | 0.658 mg/cm$^2$ | 0.0479 mg/cm$^2$ |

The ethosomal system showed an increse of 15.4 times in Kp and 13.7 times in Qs.

Example IX

| | MM39 (see Table 1) | MM blank(as above) |
|---|---|---|
| Kp= | $1.96 \times 10^{-3}$ cm*hr$^{-1}$ | $5.75 \times 10^{-5}$ cm*hr$^{-1}$ |
| $Q_{skin}$= | 0.138 mg/cm$^2$ | 0.0378 mg/cm$^2$ |

The ethosomal system showed an increse of 34 times in Kp and 3.7 times in Qs.

Example X

|     | THC (as in ex. III) | THC in PG:EtOH (1:1) |
| --- | --- | --- |
| $K_p=$ | $7.2 \times 10^{-3}$ cm*hr$^{-1}$ | $2.03 \times 10^{-3}$ cm*hr$^{-1}$ |

The ethosomal system showed an increse of 3.5 times in Kp. No significant changes in other kinetic parameters were observed

Example XI

|     | MM50G (as in ex. IV) | MM blank |
| --- | --- | --- |
| $Q_{rec}=$ (24 hours) | 0.135 mg/cm$^2$ | 0.023 mg/cm$^2$ |

The ethosomal system showed an increase of 5.9 times in Kp

Example XII

|     | ACV11 (as in ex VII) | Zovirax$^R$ |
| --- | --- | --- |
| $Q_{rec}$ (6 hours) | $2.9 \pm 1.57$ µg/cm$^2$ | $3.065 \pm 0.38$ µg/cm$^2$ |
| $Q_{skin}$ | $81.35 \pm 5.58$ µg/cm$^2$ | $18.35 \pm 8.56$ µg/cm$^2$ |

The ethosomal system showed no significant change in Kp and an increase of 4.4 times in Qs.

Example XIII

| MM122 | MM122 blank a | MM122 blank b |
| --- | --- | --- |
| 2% PL-90, 2% Minoxidil 48% EtOH 95, 28% DDW and 20% PG | 2% PL-90, 2% Minoxidil in EtOH 95 | 2% Minoxidil in EtOH 95 |
| Qrec= $3672 \pm 378$ µg/cm$^2$ (24 hours) | $217.5 \pm 118.5$ µg/cm$^2$ | $66.9 \pm 22.1$ µg/cm$^2$ |
| $Q_{skin}= 570 \pm 130.5$ µg/cm$^2$ | $139.1 \pm 25.3$ µg/cm$^2$ | $53.5 \pm 12$ µg/cm$^2$ |

The ethosomal system showed an increase of 17 times in Kp and 4.1 times in Qs relative to a 2% phospholipid solution in ethanol (blank a) and an increse of 55 times in Kp and 11 times in Qs relative to an ethanolic solution (blank b). These results clearly indicate that the ethosomal system is a much more effective penetration enhancing system than ethanol or an ethanolic solution of phospholipid.

Example XIV

|     | MND200 | Blank MND (only solvents) |
| --- | --- | --- |
| $K_p=$ | $4.27 \times 10^{-3}$ cm*hr$^{-1}$ | $1.57 \times 10^{-3}$ cm*hr$^{-1}$ |
| $Q_{skin}=$ | $2.75 \times 10$-5 mg/cm$^2$ | $2.35 \times 10$-5 mg/cm$^2$ |
| lag time = | 0:41 hrs | 2:30 hrs |

The ethosomal system showed an increse of 27 times in Kp no significant change in Qs and a decrease of 5 times in lag time.

Example XV

Figure 1:
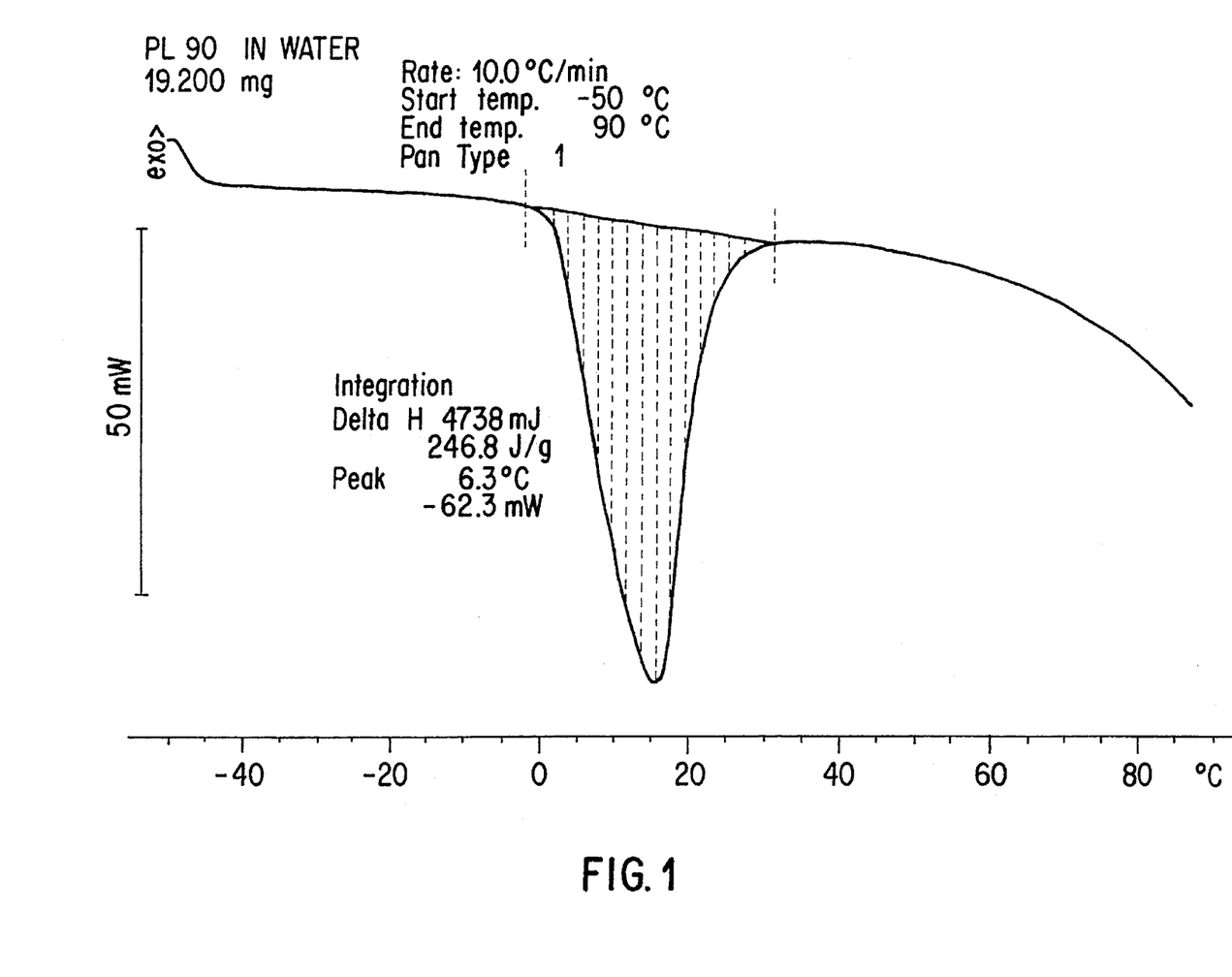
FIG. 1 is a graph showing Differential Scanning Calorimetric data of an ethosomal system containing 50% PL-90 in water (See Table 2).
Figure 2:
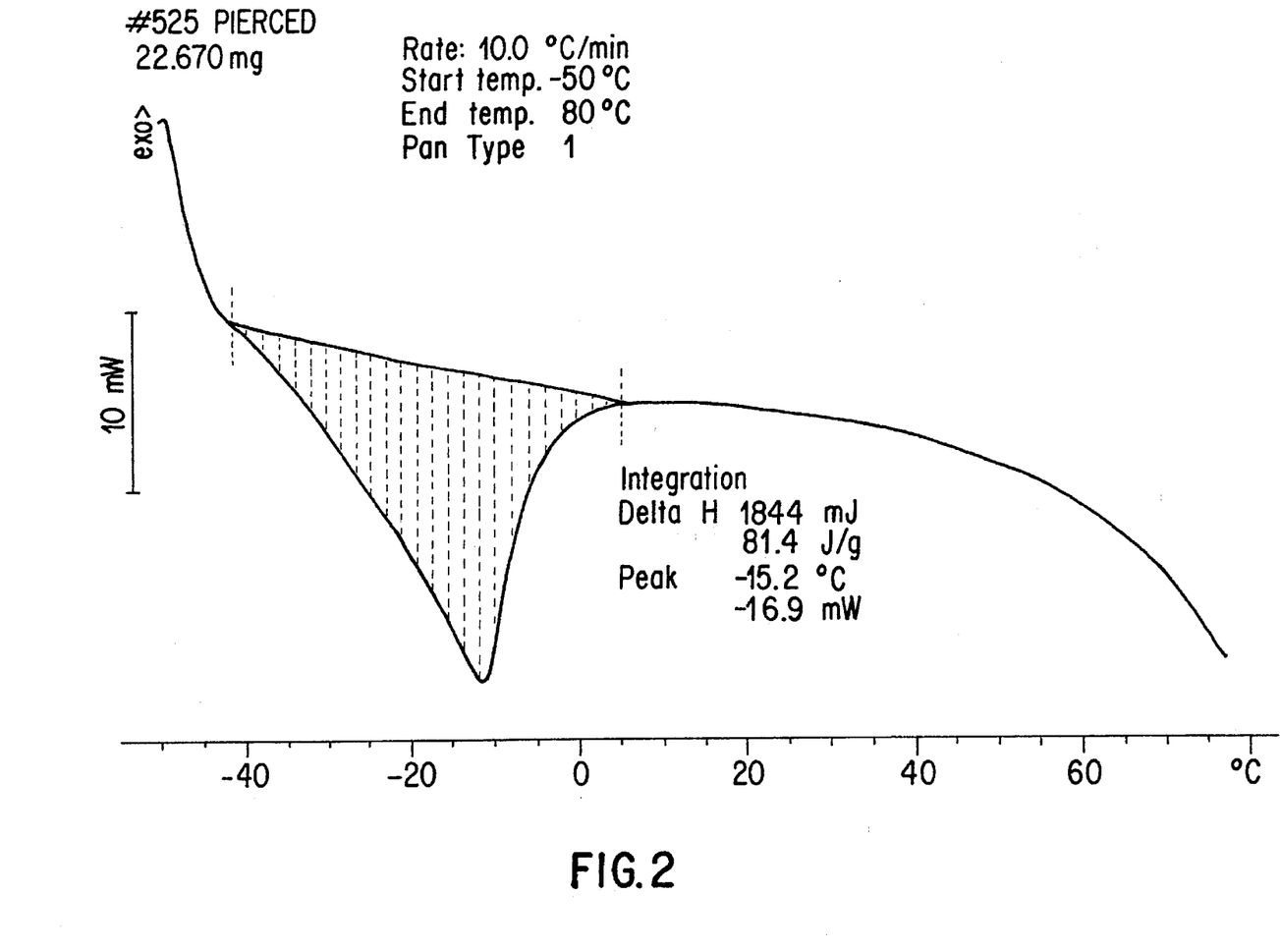
FIG. 2 is a graph showing Differential Scanning Calorimetric Data of an ethosomal system No. 525 (See Table 2).

Differential Scanning Calorimetric (DSC) data on a system containing 5% PL-90 in water and an ethosomal system No. 525 (see Table 2 for exact composition) are presented in FIGS. 1 and 2, respectively. The thermograms clearly show a decrease in Tm (transition temperature) value for the ethosomal system which indicates an increase in phospholipid vesicle's fluidity.

Example XVI

Figure 3:
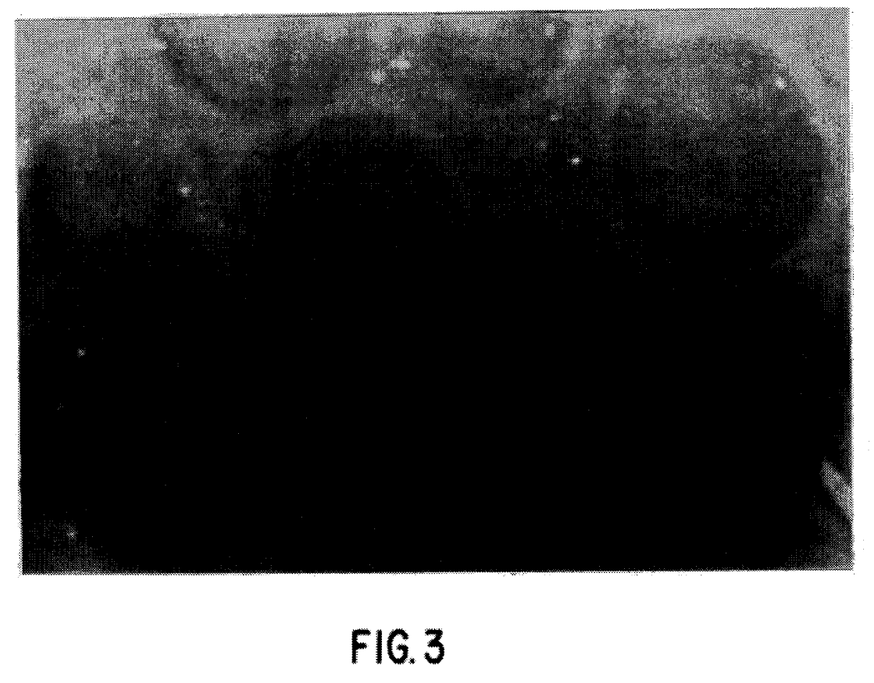
FIG. 3 is a photograph of an ethosomal system No. 510 (See Table 2).
Figure 4:
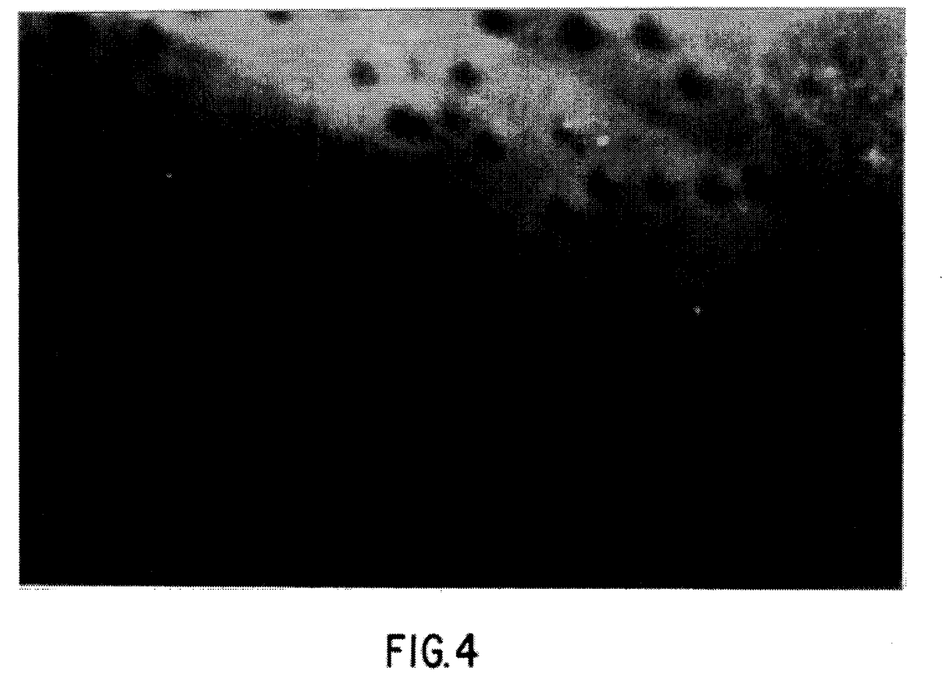
FIG. 4 is a photograph of an ethosomal system No. 529 (See Table 2).

FIGS. 3 and 4 present photographs of vesicles in ethosomal systems 510 and 529 (Table 2) as seen by means of a computerized image analyser connected to a light microscope (Cue 2 Galai- Axioscope Zeiss). These photos clearly show the presence of vesicles (ethosomes) in systems containing 20 and 34.3% ethanol, respectively.

TABLE 3

MALVERN AUTOSIZER II c for ethosomal system No. 501 (see Table 2)

sample: 501
vortex t = 22.6
aperture 200
Data from accumulation file sum of 5 blocks
Temperature 22.6 Viscosity 4.1800 Refractive Index 1.365 Angle 90.0
Particle size distribution (nm.) Graph of Distribution of mass
    10.0–12.1 +
    12.1–14.6 +
    14.6–17.7 +
    17.7–21.5 +
    21.5–26.0 +
    26.0–31.5 +
    31.5–38.2 +
    38.2–46.2 +
    46.2–56.0 +
    56.0–67.9 +
    67.9–82.2 +
    82.2–99.6 +
    99.6–120.7 +
    120.7–146.3 - - +
    146.3–177.2 +

TABLE 3-continued

MALVERN AUTOSIZER II c for ethosomal system No. 501 (see Table 2)

```
177.2–214.7  - +
214.7–260.1  - - - +
260.1–315.1  - - - - - - - - +
315.1–381.7  - - - - - - - - - - - - - - - - - - - - - +
381.7–462.5  - - - - - - - - - - - - - - - - - - - - - - - - - - - - - - - - - - - - - - - - - - - - - - - - +
462.5–560.3  - - - - - - - - - - - - - - - - - - - - - - - - - - - - - - - - - - - - - - - - - - - - - - - - - +
560.3–678.8  - - - - - - - - - - - - - - - - - - - - - - +
678.8–822.4  - - - - - - - - - - - +
822.4–996.4  - - - - - - - - +
```

TABLE 4

MALVERN AUTOSIZER II c for ethosomal system No. 503 (see Table 2)

sample: 503
vortex
22.6 temp
Data from accumulation file sum of 8 blocks
Temperature  22.7   Viscosity  3.9100   Refractive Index   1.373   Angle   90.0
Particle size distribution (nm.) Graph of Distribution of mass

```
1.6–1.8    +
1.8–2.1    - - - - - - - - - - - - +
2.1–2.4    - - - - - - - - - - - - - - - - - - - - - - +
2.4–2.8    - - - - - - - - - - - - - - - - - - - - - - - - - - - - - - - - - - +
2.8–3.2    - - - - - - - - - - - - - - - - - - - - - - - - - - - - - - - - - - - - - - - - +
3.2–3.7    - - - - - - - - - - - - - - - - - - - - - - - - - - - - - - - - - - - - - - - - - - - +
3.7–4.3    - - - - - - - - - - - - - - - - - - - - - - - - - - - - - - - - - - - - - - - - - - - +
4.3–4.9    - - - - - - - - - - - - - - - - - - - - - - - - - - - - - - - - - - - - - - - - +
4.9–5.7    - - - - - - - - - - - - - - - - - - - - - - - - - - - - - - - - - - - +
5.7–6.5    - - - - - - - - - - - - - - - - - - - - - - - - - - - - - - - - +
6.5–7.5    - - - - - - - - - - - - - - - - - - - - - - - - +
7.5–8.6    - - - - - - - - - - - - - - - - - +
8.6–10.0   - - - - - - - - - - - +
10.0–11.5  - - - - - - - +
11.5–13.2  - - - - +
13.2–15.2  - - +
15.2–17.6  - +
17.6–20.2  +
20.2–23.3  +
23.3–26.8  +
26.8–30.9  +
30.9–35.6  +
35.6–41.1  +
41.1–47.3  +
```

TABLE 5

MALVERN AUTOSIZER II c for ethosomal system No. 509 (see Table 2)

sample: 509
vortex + US
non diluted
Data from accumulation file sum of 8 blocks
Temperature  22.6   Viscosity  4.8200   Refractive Index   1.376   Angle   90.0
Particle size distribution (nm.) Graph of Distribution of mass

```
4.5–5.4    +
5.4–6.4    - - - - - - - - - - - - - - - - - - +
6.4–7.7    - - - - - - - - - - - - - - - - - - - - - - - - - - - - - - - - - - +
7.7–9.2    - - - - - - - - - - - - - - - - - - - - - - - - - - - - - - - - - - - - - - - - - - +
9.2–11.0   - - - - - - - - - - - - - - - - - - - - - - - - - - - - - - - - - - - - - - - - - - - - - - - - +
11.0–13.2  - - - - - - - - - - - - - - - - - - - - - - - - - - - - - - - - - - - - - - - - - - - - - - +
13.2–15.8  - - - - - - - - - - - - - - - - - - - - - - - - - - - - - - - - - - - - - - - - - - +
15.8–18.9  - - - - - - - - - - - - - - - - - - - - - - - - - - - - - - - - - - - - +
18.9–22.6  - - - - - - - - - - - - - - - - - - - - - - - - - - - - - +
22.6–27.1  - - - - - - - - - - - - - - - - - - - - - - +
27.1–32.4  - - - - - - - - - - - - - - - +
32.4–38.8  - - - - - - - - - +
38.8–46.4  - - - - - +
```

TABLE 5-continued

MALVERN AUTOSIZER II c for ethosomal system No. 509 (see Table 2)

```
46.4–55.6    - - - +
55.6–66.6    - - +
66.7–79.7    - +
79.7–95.5    +
95.5–114.3   +
114.3–136.8  +
136.8–163.8  +
163.8–196.2  +
196.2–234.9  +
234.9–281.2  +
281.2–336.7  +
Size Class    % by Intensity    % by mass    % by number
```

TABLE 6

MALVERN AUTOSIZER II c for ethosomal system No. 510 (see Table 2)

sample: 510
vortex + US
non diluted
Data from accumulation file sum of 68 blocks
Temperature  22.6  Viscosity  4.6400  Refractive Index  1.374  Angle  90.0
Particle size distribution (nm.) Graph of Distribution of mass

```
17.4–21.1    +
21.1–25.6    +
25.6–31.0    +
31.0–37.6    +
37.6–45.5    - - - - - - - - - - - - - - - - - - - - - - - - - - - - - - - - - - - - - - - - - - - - - - +
45.5–55.1    - - - - - - - - - - - - - - - - - - - - - - - - - - - - - - - - - - - - - +
55.1–66.8    +
66.8–80.9    +
80.9–98.0    +
98.0–118.8   +
118.8–143.9  +
143.9–174.3  +
174.3–211.2  +
211.2–255.9  - +
255.9–310.0  +
310.0–375.6  +
375.6–455.0  - - - - - - - - - - - +
455.0–551.3  - - - - - - - - - - - - - - - - - - - - - - +
551.3–667.9  - - - - - - - - - - - - - - - - - - - - - - - +
667.9–809.2  - - - - - - - - - - - - - - - - - - - - - - - - - - - - - +
809.2–980.3  - - - - - - - - - - - - - - - - - - - - - - - - - - - - - - - - - - - - - +
980.3–1187.7 - - - - - - - - - - - - - - - - - - - - - - - - - - - - - - - - - - - - - - +
1187.7–1438.9 - - - - - - - - - - - - - - - - - - - - - - - - - +
1438.9–1743.3 - - - - - - - - - - - - - - - - - - +
```

I claim:

1. A liposomal composition for medical or cosmetic use, for topical application to the skin, resulting in the transdermal passage or introduction of an active ingredient into the skin, which composition contains vesicles in a size range up to 1743 nm, which composition comprises from 0.5% to 10% phospholipids, from 20% to 50% of ethanol, from 0 to 20% propylene glycol, at least 20% water and at least one active ingredient where the combined ethanol and propylene glycol content does not exceed 70%.

2. A composition according to claim 1, comprising 22 to 70% of a combination of the ethanol and propylene glycol, and more than 20% water.

3. A composition according to claim 1, where the phospholipids comprise at least one member selected from the group consisting of phosphatidylcholine, (P C), hydrogenated P C, phosphatidic acid (P A), phosphatidylserine (P S), phosphatidylethanolamine (P E), phosphatidyglycerol (P P G) and phosphatidylinositol (P I).

4. A composition according to claim 1, where the amount of ethanol is between 20 and 50 weight-% of the composition, the content of water being at least about 25 weight-%.

5. A composition according to claim 1, in which the active ingredient is a member selected from the group consisting of peptides, hormones, anti-aging agents, tanning agents, vitamins, antiviral drugs, plant extracts, glycosides, alkaloids, anxiolytics, antiepileptics, antifungals, non-steroidal anti-inflammatory drugs, antihypertensive agents, corticosteroids, minoxidil, cannabinoids, antinytotics, antibiotics and hydroxy acids.

* * * * *